Feb. 4, 1964 C. FISCHER Plant Pat. 2,355
GLADIOLUS PLANT
Filed Sept. 18, 1962
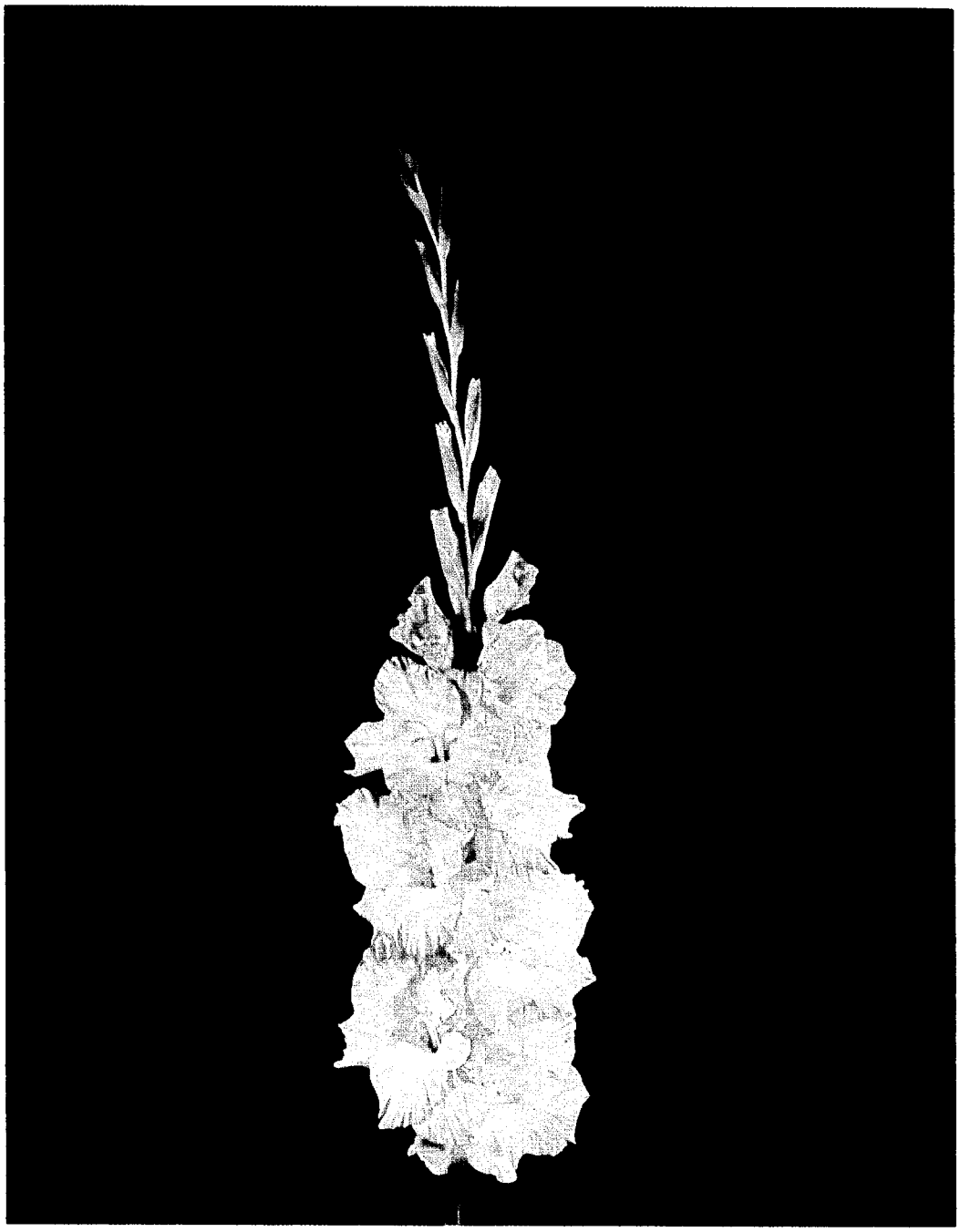
Inventor.
Carl Fischer
By: Robb & Robb
Attorneys.

United States Patent Office

Plant Pat. 2,355
Patented Feb. 4, 1964

2,355
GLADIOLUS PLANT

Carl Fischer, St. Charles, Minn., assignor to Imperial Flowers Limited, Leamington, Ontario, Canada, a corporation of Canada Filed Sept. 18, 1962, Ser. No. 224,584
1 Claim. (Cl. Plt.—85)

The present invention relates to a new and distinct variety of gladiolus plant which was originated by me by crossing the variety "Maytime" (Plant Patent No. 1,591) with the variety known as "Royal Stewart" (Plant Patent No. 1,339), the former being the seed parent and the latter being the pollen parent.

As the result of this breeding, I have produced a new and improved gladiolus variety having a unique combination of characteristics which distinguish it from its parents, as well as from all other varieties of which I am aware, as evidenced by the following features which are outstanding therein:

(1) Robust and vigorous habits of plant growth;
(2) An early flowering habit;
(3) Large flower size;
(4) The ability to open well from tight buds; and
(5) A distinctive and attractive Geranium Lake general color tonality of the flowers, said flowers having large white throats and prominent white midribs.

My new variety resembles the parent variety "Maytime" more than any other, but differs principally therefrom by the ability of the flowers to open better from tight buds, larger individual florets, and shorter but more developed flowerheads.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Extremely rugged; prolific propagator; averages 60 inches in height.

Blooming habit: Early bloomer in the northern latitudes of the United States; comes into bloom from large bulbs in from 70 to 75 days.

Stems: Straight; willowy; hollow at base.

*Diameter at base.*—About ⅜ inch.

*Color (just above bulb).*—Mallow Purple, Plate 630.

Foliage: Droopy; leaves average about 40 inches tall; average leaves range from about 1½ inches to 1¾ inches wide. Color—healthy green.

Disease resistance: Unusually good resistance to Fusarium yellows, Sclerotina dry rot and Septoria leaf spot, as determined by comparison with other varieties grown in my fields near St. Charles, Minnesota, in irrigated black loam soil.

Corms (bulbs): Heavy; plump; round; high-crowned; average about 2½ inches in diameter; well-husked with heavy and thick husks. Color of flesh—between Amber Yellow, Plate 505 and Amber Yellow, Plate 505/2.

*Flower*

Spike: Tall; flowerhead averages about 25 inches long; bears from 18 to 20 buds, with from 8 to 10 buds open at once and with 6 to 7 buds showing color.

Bud:

*Size.*—About 2½ inches long when opening.

*Opening.*—6 to 7 buds show color at one time; open very well.

Flower:

*Arrangement.*—Florets are formally placed in a double row on the stem and always face forward.

*Size.*—Individual lower florets average about 5½ inches in diameter, with upper florets being progressively smaller.

*Form.*—Florets are round and ruffled.

*Keeping qualities.*—Keeps well.

Petals:

*Shape.*—Round, ruffled; recurved.

*Size.*—Outer petals—about 2¼ inches by 2½ inches. Lip petal—from about 1½ inches to 1¾ inches wide.

*Aspect.*—Average substance; smooth surface.

*Fragrance.*—None.

*Color.*—Basic color is Geranium Lake, with deepest color being Geranium Lake, Plate 20 occurring at edges of petals, with color shading through Geranium Lake, Plate 20/1 to Geranium Lake, Plate 20/2 at base of upper petals; florets have large white throats and each petal has prominent white midrib; reverse of florets is Geranium Lake, Plate 20 in general effect, with base of calyx being Magenta, Plate 27.

*Reproductive Organs*

Stamens: Color—light purple.

Pistil: Color—faint Geranium Lake, Plate 20/3.

I claim:

A new and distinct variety of gladiolus plant, substantially as herein shown and described, characterized particularly as to novelty by robust and vigorous habits of plant growth, an early flowering habit, large flower size, the ability to open well from tight buds, and a distinctive and attractive Geranium Lake general color tonality of the flowers, said flowers having large, white throats, and the flower petals having prominent white midribs.

No references cited.